US 8,133,437 B2

(12) United States Patent
Scalzo et al.

(10) Patent No.: US 8,133,437 B2
(45) Date of Patent: *Mar. 13, 2012

(54) METHOD OF PREPARING AN ANTIMICROBIAL PACKAGED MEDICAL DEVICE

(75) Inventors: Howard Scalzo, Kenilworth, NJ (US); Jerome A. Fischer, Warren, NJ (US); Stephen Rothenburger, Neshanic Station, NJ (US); Robert Cerwin, Pipersville, PA (US); James R. McDivitt, Flemington, NJ (US)

(73) Assignee: Ethicon, Inc., Somerville, NJ (US)

(*) Notice: Subject to any disclaimer, the term of this patent is extended or adjusted under 35 U.S.C. 154(b) by 1464 days.

This patent is subject to a terminal disclaimer.

(21) Appl. No.: 11/301,364

(22) Filed: Dec. 13, 2005

(65) Prior Publication Data

US 2006/0091034 A1   May 4, 2006

(51) Int. Cl.
*A61L 9/00* (2006.01)
*A61L 2/00* (2006.01)
*A61L 2/18* (2006.01)
*A61L 2/20* (2006.01)
*B01J 7/00* (2006.01)
*B65B 11/58* (2006.01)
*A61B 17/06* (2006.01)
*A61L 17/00* (2006.01)

(52) U.S. Cl. ............... 422/29; 422/28; 422/33; 422/292; 422/294; 422/305; 53/449; 206/63.3; 606/228

(58) Field of Classification Search .................... 422/28, 422/29; 600/228; 53/449; 206/63.3
See application file for complete search history.

(56) References Cited

U.S. PATENT DOCUMENTS 809,725 A   1/1906 Neff
(Continued)

FOREIGN PATENT DOCUMENTS

AU    52834/86 B    2/1987
(Continued)

OTHER PUBLICATIONS

Database EMBASE on STN, AN 2003062. Barbolt T.A. "Chemistry and Safety of Triclosan, and its Use as an Antimicrobial Coating on Coated VICRYL. Plus Antibacterial Suture (Coated Polyglactin 910 Suture with Triclosan)". Surgical Infections, May 2002, vol. 3, No. 3, Supplement 1, pp. S-45-S-53, see abstract.
(Continued)

*Primary Examiner* — Kevin C. Joyner
*Assistant Examiner* — Regina M. Yoo
(74) *Attorney, Agent, or Firm* — Roberts Mlotkowski Safran & Cole, P.C.

(57) ABSTRACT

A method for making an antimicrobial suture comprising the steps of positioning an antimicrobial agent source within a package comprising an inner surface, said antimicrobial agent being selected from the group consisting of halogenated hydroxyl ethers, acyloxydiphenyl ethers, and combinations thereof; positioning a medical device within the package; and subjecting the package, the antimicrobial agent source and the medical device to time, temperature and pressure conditions sufficient to vapor transfer an effective amount of the antimicrobial agent from the antimicrobial agent source to the medical device, thereby substantially inhibiting bacterial colonization on the medical device. Alternatively, the packaged medical device is produced according to the steps of positioning a medical device within a package; exposing the package having the medical device to an antimicrobial agent source; and subjecting the package having the medical device and the antimicrobial agent source to time, temperature and pressure conditions sufficient to transfer an effective amount of the antimicrobial agent from the antimicrobial agent source to the medical device within the package, thereby substantially inhibiting bacterial colonization on the medical device.

13 Claims, 1 Drawing Sheet

U.S. PATENT DOCUMENTS

| | | | |
|---|---|---|---|
| 2,917,878 A | 12/1959 | Carnarius et al. | |
| 2,947,282 A | 8/1960 | Brown | |
| 3,202,273 A | 8/1965 | Riall | |
| 3,613,879 A | 10/1971 | Kemble | |
| 3,629,477 A | 12/1971 | Model et al. | |
| 3,642,003 A | 2/1972 | Kurtz | |
| 3,726,057 A | 4/1973 | Kemble | |
| 3,815,315 A | 6/1974 | Glick | |
| 3,862,304 A | 1/1975 | Kurtz | |
| 3,896,812 A | 7/1975 | Kurtz | |
| 3,939,971 A | 2/1976 | Tulis | |
| 3,991,766 A | 11/1976 | Schmitt et al. | |
| 4,024,871 A | 5/1977 | Stephenson | |
| 4,105,034 A | 8/1978 | Shalaby et al. | |
| 4,230,663 A * | 10/1980 | Forstrom et al. | 422/33 |
| 4,476,590 A | 10/1984 | Scales et al. | |
| 4,482,053 A | 11/1984 | Alpern et al. | |
| 4,603,538 A | 8/1986 | Shave | |
| 4,605,564 A | 8/1986 | Kulla et al. | |
| 4,615,705 A | 10/1986 | Scales et al. | |
| 4,728,323 A | 3/1988 | Matson | |
| 4,846,844 A | 7/1989 | De Leon et al. | |
| 4,853,978 A | 8/1989 | Stockum | |
| 4,856,504 A | 8/1989 | Yamamoto et al. | |
| 4,946,043 A | 8/1990 | Roshdy et al. | |
| 4,952,419 A | 8/1990 | De Leon et al. | |
| 5,019,096 A | 5/1991 | Fox, Jr. et al. | |
| 5,037,429 A | 8/1991 | Hermes et al. | |
| 5,052,551 A | 10/1991 | Cerwin et al. | |
| 5,066,328 A | 11/1991 | Zlotnik | |
| 5,091,442 A | 2/1992 | Milner | |
| 5,154,283 A | 10/1992 | Brown | |
| 5,165,913 A | 11/1992 | Hill et al. | |
| 5,180,605 A | 1/1993 | Milner | |
| 5,261,421 A | 11/1993 | Milner | |
| 5,284,240 A | 2/1994 | Alpern et al. | |
| 5,295,979 A | 3/1994 | DeLaurentis et al. | |
| 5,359,831 A | 11/1994 | Brown et al. | |
| 5,468,252 A | 11/1995 | Kaplan et al. | |
| 5,468,562 A | 11/1995 | Farivar et al. | |
| 5,474,797 A | 12/1995 | Sioshansi et al. | |
| 5,518,730 A | 5/1996 | Fuisz | |
| 5,529,175 A | 6/1996 | Brunken | |
| 5,534,288 A | 7/1996 | Gruskin et al. | |
| 5,556,699 A | 9/1996 | Niira et al. | |
| 5,562,211 A | 10/1996 | Simons et al. | |
| 5,607,681 A | 3/1997 | Galley et al. | |
| 5,708,023 A | 1/1998 | Modak et al. | |
| 5,722,992 A | 3/1998 | Goldmann | |
| 5,756,145 A | 5/1998 | Darouiche | |
| 5,772,640 A | 6/1998 | Modak et al. | |
| 5,804,628 A | 9/1998 | Busnel et al. | |
| 5,853,745 A | 12/1998 | Darouiche | |
| 5,868,244 A | 2/1999 | Ivanov et al. | |
| 5,889,075 A | 3/1999 | Roby et al. | |
| 5,902,283 A | 5/1999 | Darouiche | |
| 5,906,273 A | 5/1999 | Pohle et al. | |
| 5,906,825 A | 5/1999 | Seabrook, Jr. et al. | |
| 5,945,153 A | 8/1999 | Deamaley | |
| 5,965,610 A | 10/1999 | Modak et al. | |
| 5,968,207 A | 10/1999 | Li | |
| 5,985,934 A | 11/1999 | Gaffney et al. | |
| 5,997,815 A | 12/1999 | Anders et al. | |
| 6,034,010 A | 3/2000 | Cartwright et al. | |
| 6,037,386 A | 3/2000 | Modak et al. | |
| 6,047,815 A | 4/2000 | Cerwin et al. | |
| 6,083,208 A | 7/2000 | Modak et al. | |
| 6,087,415 A | 7/2000 | Vamderlaan et al. | |
| 6,093,414 A | 7/2000 | Capelli | |
| 6,106,505 A | 8/2000 | Modak et al. | |
| 6,165,920 A | 12/2000 | Rubin et al. | |
| 6,224,579 B1 | 5/2001 | Modak et al. | |
| 6,238,686 B1 | 5/2001 | Burrell et al. | |
| 6,260,699 B1 | 7/2001 | Kaplan et al. | |
| 6,315,788 B1 | 11/2001 | Roby | |
| 6,481,568 B1 | 11/2002 | Cerwin et al. | |
| 6,494,898 B1 | 12/2002 | Roby et al. | |
| 6,495,100 B1 | 12/2002 | Lin et al. | |
| 6,706,024 B2 | 3/2004 | Modak et al. | |
| 6,837,027 B2 | 1/2005 | Hickey | |
| 6,916,480 B2 * | 7/2005 | Anderson et al. | 424/404 |
| 7,275,640 B2 | 10/2007 | Bourne et al. | |
| 7,513,093 B2 * | 4/2009 | Scalzo et al. | 53/449 |
| 7,651,661 B2 * | 1/2010 | Raad et al. | 422/28 |
| 2001/0010016 A1 | 7/2001 | Modak et al. | |
| 2001/0016589 A1 | 8/2001 | Modak et al. | |
| 2001/0024661 A1 | 9/2001 | Modak et al. | |
| 2002/0055759 A1 | 5/2002 | Shibuya | |
| 2003/0108761 A1 | 6/2003 | Eddlemon | |
| 2003/0138347 A1 * | 7/2003 | Lin | 422/28 |
| 2004/0220614 A1 * | 11/2004 | Scalzo et al. | 606/228 |
| 2006/0231443 A1 | 10/2006 | Jonasson et al. | |
| 2008/0171972 A1 | 7/2008 | Stopek | |
| 2009/0301033 A1 | 12/2009 | Scalzo et al. | |
| 2010/0036359 A1 | 2/2010 | Stopek et al. | |
| 2010/0078336 A1 | 4/2010 | Reyhan et al. | |
| 2010/0116694 A1 | 5/2010 | Stopek et al. | |

FOREIGN PATENT DOCUMENTS

| | | | |
|---|---|---|---|
| CA | 2185056 | * | 3/1997 |
| CN | 2115083 U | * | 9/1992 |
| CN | 21909968 Y | | 9/1992 |
| CN | 1125622 A | * | 7/1996 |
| EP | 0 471 441 A1 | * | 2/1992 |
| EP | 0470443 A2 | | 2/1992 |
| EP | 0761243 A1 | | 3/1997 |
| EP | 1159972 A2 | | 12/2001 |
| GB | 0 809 725 | * | 3/1959 |
| JP | 49-111794 | | 10/1974 |
| JP | 8-164190 A | | 6/1996 |
| JP | 10-504756 | | 5/1998 |
| JP | 11-500330 | | 1/1999 |
| JP | 2000-237289 | | 5/2000 |
| TW | 408011 B | * | 10/2000 |
| TW | 446822 B | * | 7/2001 |
| WO | WO 98/09667 | | 3/1998 |
| WO | 00/44414 | * | 8/2000 |
| WO | WO 01/28601 A1 | | 4/2001 |
| WO | 2008/045338 A2 | | 4/2008 |

OTHER PUBLICATIONS

Database ACS on STN, AN 133: 366471. Anuzis et al. "Acetate antimicrobial threads". LT 4568 B, Oct. 25, 1999, abstract.

Josephine J. Braid et al., "The antibacterial activity of triclosan-impregnated storage boxes against *Staphylococcus aureus, Escherichia coli, Pseudomonas aeruginosa, Bacillus cereus* and *Shewanella putrefaciens* in conditions simulating domestic use" Journal of Antimocrobial Chemotherapy (2002) vol. 49 pp. 87-94.

* cited by examiner

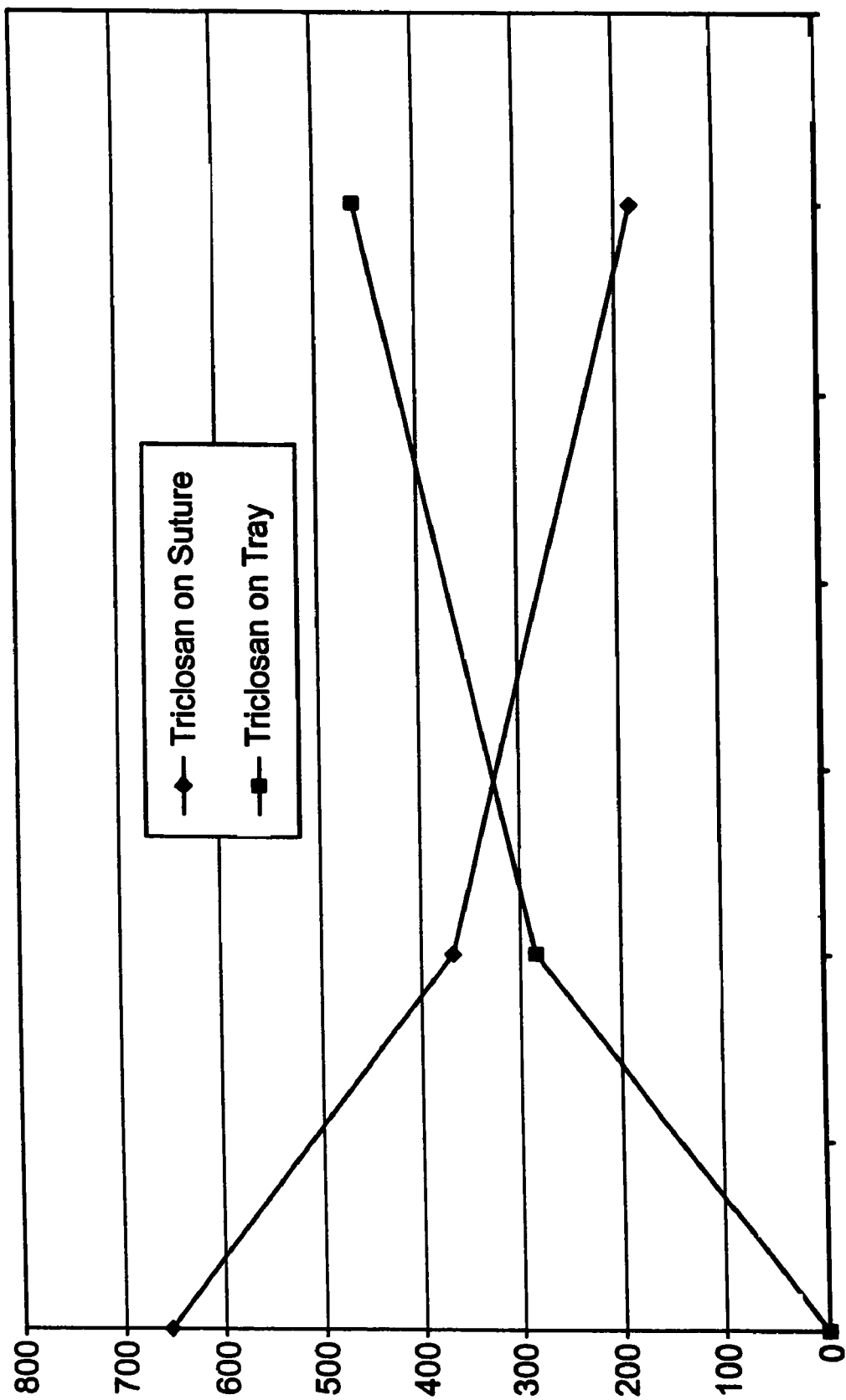

METHOD OF PREPARING AN ANTIMICROBIAL PACKAGED MEDICAL DEVICE

CROSS-REFERENCE TO RELATED APPLICATIONS

This application claims the benefit of U.S. Ser. No. 10/603,317 filed on Jun. 25, 2003 and Ser. No. 10/808,669 filed on Mar. 25, 2004. U.S. Ser. No. 10/808,669 is a continuation-in-part of U.S. Ser. No. 10/603,317, which is a continuation-in-part of U.S. Ser. No. 10/367,497, filed on Feb. 15, 2003, which claimed the benefit of U.S. Provisional Application No. 60/416,114, filed on Oct. 4, 2002. This application is related to U.S. Ser. No. 10/367,565, filed on 15 Feb. 2003.

FIELD OF THE INVENTION

The present invention relates to an antimicrobial medical device and an antimicrobial packaged medical device and their methods of making.

BACKGROUND OF THE INVENTION

Each year, patients undergo a vast number of surgical procedures in the United States. Current data shows about twenty-seven million procedures are performed per year. Post-operative or surgical site infections ("SSIs") occur in approximately two to three percent of all cases. This amounts to more than 675,000 SSIs each year.

The occurrence of SSIs is often associated with bacteria that can colonize on implantable medical devices used in surgery. During a surgical procedure, bacteria from the surrounding atmosphere may enter the surgical site and attach to the medical device. Specifically, bacteria can spread by using the implanted medical device as a pathway to surrounding tissue. Such bacterial colonization on the medical device may lead to infection and trauma to the patient. Accordingly, SSIs may significantly increase the cost of treatment to patients.

Implantable medical devices that contain antimicrobial agents applied to or incorporated within have been disclosed and/or exemplified in the art. Examples of such devices are disclosed in European Patent Application No. EP 0 761 243. Actual devices exemplified in the application include French Percuflex catheters. The catheters were dip-coated in a coating bath containing 2,4,4'-tricloro-2-hydroxydiphenyl ether (Ciba Geigy Irgasan (DP300)) and other additives. The catheters then were sterilized with ethylene oxide and stored for thirty days. Catheters coated with such solutions exhibited antimicrobial properties, i.e., they produced a zone of inhibition when placed in a growth medium and challenged with microorganism, for thirty days after being coated. It is not apparent from the application at what temperature the sterilized, coated catheters were stored.

Most implantable medical devices are manufactured, sterilized and contained in packages until opened for use in a surgical procedure. During surgery, the opened package, packaging components contained therein, and the medical device are exposed to the operating room atmosphere, where bacteria from the air may be introduced. Incorporating antimicrobial properties into the package and the packaging components substantially prevents bacterial colonization on the package and components once the package has been opened. The antimicrobial package and packaging components, in combination with the incorporation of antimicrobial properties onto the medical device itself would substantially ensure an antimicrobial environment about the sterilized medical device.

SUMMARY OF THE INVENTION

The present invention relates to antimicrobial medical devices and antimicrobial packaged medical devices and methods for preparing them. In accordance with embodiments of the present invention, an antimicrobial agent source is utilized. The medical device, with or without one or more packaging component, is positioned within a package, and upon being subjected to sufficient conditions, a portion of the antimicrobial agent from the antimicrobial agent source transfers to the package, the packaging component (if utilized) and the medical device. The transfer of the antimicrobial agent is in an amount sufficient to inhibit bacterial growth on the package, the packaging component (if utilized) and the medical device.

In accordance with various embodiments of the present invention, the package may contain an antimicrobial agent source, may have an antimicrobial agent source attached to the inner surface of the package, or may have an antimicrobial agent source that is integral with one or more packaging component in the package or with the package itself. Alternatively, the medical device may be positioned within a package, and the package having the medical device is exposed to an external antimicrobial agent source. In these embodiments, the medical device is positioned within the package and may initially be free of an antimicrobial agent or may initially comprise one or more surfaces having an antimicrobial agent disposed thereon. The package, the antimicrobial agent source and the medical device are then subjected to time, temperature and pressure conditions sufficient to vapor transfer an effective amount of the antimicrobial agent from the antimicrobial agent source to the inner surface of the package and the medical device, thereby substantially inhibiting bacterial colonization on the medical device.

The present invention is also directed to a method for making an antimicrobial medical device comprising the step of positioning an antimicrobial agent source in a package having a medical device, attaching an antimicrobial agent source to the inner surface of a package having a medical device, or providing an antimicrobial agent source that is integral with one or more packaging component in the package having the medical device or with the package itself. In these embodiments, the medical device that is positioned within the package may initially be free of an antimicrobial agent or may initially comprise one or more surfaces having an antimicrobial agent disposed thereon. The package, the antimicrobial agent source and the medical device are then subjected to time, temperature and pressure conditions sufficient to vapor transfer an effective amount of the antimicrobial agent from the antimicrobial agent source to the medical device, thereby substantially inhibiting bacterial colonization on the medical device.

BRIEF DESCRIPTION OF THE DRAWING

FIG. 1 is a graph illustrating the transfer of an antimicrobial agent from the medical device to a packaging component at 55° C. as a function of time.

DETAILED DESCRIPTION OF EMBODIMENTS OF THE INVENTION

Packaged Antimicrobial Medical Device

The medical devices described herein are generally implantable medical devices and implants, including but not limited to mono and multifilament sutures, surgical meshes such as hernia repair mesh, hernia plugs, brachy seed spacers, suture clips, suture anchors, adhesion prevention meshes and films, and suture knot clips. Also included are implantable medical devices that are absorbable and non-absorbable. An absorbable polymer is defined as a polymer that will degrade and be absorbed by the body over a period of time when exposed to physiological conditions. Absorbable medical devices typically are formed from generally known, conventional absorbable polymers including but not limited to glycolide, lactide, copolymers of glycolide, or mixtures of polymers, such as polydioxanone, polycaprolactone, oxidized regenerated cellulose and equivalents thereof. Preferably, the polymers include polymeric materials selected from the group consisting of greater than about 70% polymerized glycolide, greater than about 70% polymerized lactide, polymerized 1,4-dioxan-2-one, greater than about 70% polypeptide, copolymers of glycolide and lactide, greater than about 70% cellulosics and cellulosic derivatives. Preferably, absorbable medical devices are made from polydioxanone, poliglecaprone, or a glycolide/lactide copolymer. Examples of absorbable medical device include mono and multifilament sutures. The multifilament suture includes sutures wherein a plurality of filaments is formed into a braided structure. Examples of non-absorbable medical devices include mono and multifilament sutures, surgical meshes such as hernia repair mesh, hernia plugs and brachy seed spacers, which may be polymeric or nonpolymeric. Non-absorbable medical devices may be made in whole or in part from polymeric materials that include, but are not limited to, polyolefins such as polypropylene; polyamides such as nylon; chlorinated and/or fluorinated hydrocarbons such as Teflon® material; or polyesters such as Dacron® synthetic polyesters; or from non-polymeric materials that include, but are not limited to, silks, collagen, stainless steel, titanium, cobalt chromium alloy, nitinol. Preferably, the non-absorbable medical devices are made from nylon or polypropylene.

Suitable antimicrobial agents may be selected from, but are not limited to, halogenated hydroxyl ethers, acyloxydiphenyl ethers, or combinations thereof. In particular, the antimicrobial agent may be a halogenated 2-hydroxydiphenyl ether and/or a halogenated 2-acyloxy diphenyl ether, as described in U.S. Pat. No. 3,629,477, and represented by the following formula:

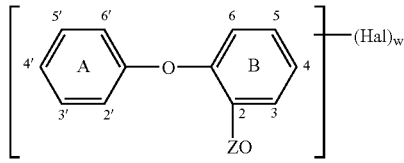

In the above formula, each Hal represents identical or different halogen atoms, Z represents hydrogen or an acyl group, and w represents a positive whole number ranging from 1 to 5, and each of the benzene rings, but preferably ring A can also contain one or several lower alkyl groups which may be halogenated, a lower alkoxy group, an allyl group, a cyano group, an amino group, or lower alkanoyl group. Preferably, methyl or methoxy groups are among the useful lower alkyl and lower alkoxy groups, respectively, as substituents in the benzene rings. A halogenated lower alkyl group, trifluoromethyl group is preferred.

Antimicrobial activity similar to that of the halogen-o-hydroxydiphenyl ethers of the above formula is also attained using the O-acyl derivatives thereof which partially or completely hydrolyze under the conditions for use in practice. The esters of acetic acid, chloroacetic acid, methyl or dimethyl carbamic acid, benzoic acid, chlorobenzoic acid, methylsulfonic acid and chloromethylsulfonic acid are particularly suitable.

One particularly preferred antimicrobial agent within the scope of the above formula is 2,4,4'-trichloro-2'-hydroxydiphenyl ether, commonly referred to as triclosan (manufactured by Ciba Geigy under the trade name Irgasan DP300 or Irgacare MP). Triclosan is a broad-spectrum antimicrobial agent that has been used in a variety of products, and is effective against a number of organisms commonly associated with SSIs. Such microorganisms include, but are not limited to, genus *Staphylococcus, Staphylococcus epidermidis, Staphylococcus aureus*, methicillin-resistant *Staphylococcus epidermidis*, methicillin-resistant *Staphylococcus aureus*, and combinations thereof.

In addition to the antimicrobial agents described above, the medical device optionally may have a biocide, a disinfectant and/or an antiseptic, including but not limited to alcohols such as ethanol and isopropanol; aldehydes such as glutaraldehyde and formaldehyde; anilides such as triclorocarbanilide; biguanides such as chlorhexidine; chlorine-releasing agents such as sodium hypochlorite, chlorine dioxide and acidified sodium chlorite; iodine-releasing agents such as povidone-iodine and poloxamer-iodine; metals such as silver nitrate, silver sulfadiazine, other silver agents, copper-8-quinolate and bismuth thiols; peroxygen compounds such as hydrogen peroxide and peracetic acid; phenols; quaternary ammonium compounds such as benzalkonium chloride, cetrimide and ionenes-polyquaternary ammonium compounds. The medical device optionally may have antibiotics, including but not limited to penicillins such as amoxicillin, oxacillin and piperacillin; cephalosporins parenteral such as cefazolin, cefadroxil, cefoxitin, cefprozil, cefotaxime and cefdinir; monobactams such as aztreonam; beta-lactamase inhibitors such as clavulanic acid sulbactam; glycopeptide such as vancomycin; polymixin; quinolones such as nalidixic acid, ciprofloxacin and levaquin; metranidazole; novobiocin; actinomycin; rifampin; aminoglycosides such as neomycin and gentamicin; tetracyclines such as doxycycline; chloramphenicol; macrolide such as erythromycin; clindamycin; sulfonamide such as sulfadiazine; trimethoprim; topical antibiotics; bacitracin; gramicidin; mupirocin; and/or fusidic acid. Optionally, the medical device may have antimicrobial peptides such as defensins, magainin and nisin; lytic bacteriophage; surfactants; adhesion blockers such as antibodies, oligosaccharides and glycolipids; oligonucleotides such as antisense RNA; efflux pump inhibitors; photosensitive dyes such as porphyrins; immune modulators such as growth factors, interleukins, interferons and synthetic antigens; and/or chelators such as EDTA, sodium hexametaphosphate, lactoferrin and transferrin.

The antimicrobial agent may be delivered to the medical device from an antimicrobial agent source that is positioned within or attached to the inner surface of a package. Specifically, the antimicrobial agent is transferred from the antimicrobial agent source to the medical device when the package, the antimicrobial agent source and the medical device are subjected to time, temperature and pressure conditions, as described below. For example, the antimicrobial agent source may be an antimicrobial agent-loaded paper reservoir, an antimicrobial agent-loaded porous pouch reservoir, an antimicrobial agent-loaded plastic reservoir, an antimicrobial agent-loaded sponge or foam reservoir, an antimicrobial agent-loaded tape, or an antimicrobial agent-loaded tablet. Alternatively, the antimicrobial agent source may be integral with the package itself, i.e., antimicrobial agent incorporated into or on the package itself, such as but not limited to, applied directly on the inner surface of the package. Where the antimicrobial agent source is in a paper or plastic reservoir, such reservoir may be integral with one or more packaging component in the package.

Additionally, the medical device may optionally have a coating thereon, and/or may optionally comprise one or more surfaces having an antimicrobial agent disposed thereon prior to any transfer of antimicrobial agent to the medical device from the antimicrobial agent source. For example, it is advantageous to apply a coating composition having an antimicrobial agent therein to the surface of the medical device. Examples of medical devices, as well as coatings that may be applied thereto, may be found in U.S. Pat. Nos. 4,201,216, 4,027,676, 4,105,034, 4,126,221, 4,185,637, 3,839,297, 6,260,699, 5,230,424, 5,555,976, 5,868,244, and 5,972,008, each of which is hereby incorporated herein in its entirety. As disclosed in U.S. Pat. No. 4,201,216, the coating composition may include a film-forming polymer and a substantially water-insoluble salt of a $C_6$ or higher fatty acid. As another example, an absorbable coating composition that may be used for an absorbable medical device may include poly(alkylene oxylates) wherein the alkylene moieties are derived from $C_6$ or mixtures of $C_4$ to $C_{12}$ diols, which is applied to a medical device from a solvent solution, as disclosed in U.S. Pat. No. 4,105,034. The coating compositions may include a polymer or copolymer, which may include lactide and glycolide, as a binding agent. The coating compositions may also include calcium stearate, as a lubricant; and an antimicrobial agent. The coating may be applied to the device by solvent-based coating techniques, such as dip coating, spray coating, or suspended drop coating, or any other coating means.

Absorbable medical devices are moisture sensitive, that is, they are devices that will degrade if exposed to moisture in the atmosphere or in the body. It is known by those of ordinary skill in the art that medical devices made from absorbable polymers may deteriorate and lose their strength if they come into contact with water vapor prior to use during surgery. For instance, the desirable property of in vivo tensile strength retention for sutures will be rapidly lost if the sutures are exposed to moisture for any significant period of time prior to use. Therefore, it is desirable to use a hermetically sealed package for absorbable medical devices. A hermetically sealed package is defined herein to mean a package made of a material that serves as both a sterile barrier and a gas barrier, i.e., prevents or substantially inhibits moisture and gas permeation.

Materials useful for constructing the package for absorbable medical devices, for example, include single and multi-layered conventional metal foil products, often referred to as heat-sealable foils. These types of foil products are disclosed in U.S. Pat. No. 3,815,315, which is hereby incorporated by reference in its entirety. Another type of foil product that may be utilized is a foil laminate referred to in the field of art as a peelable foil. Examples of such peelable foil and substrates are disclosed in U.S. Pat. No. 5,623,810, which is hereby incorporated by reference in its entirety. If desired, conventional non-metallic polymer films in addition to or in lieu of metal foil may be used to form the package for absorbable medical devices. Such films are polymeric and may include conventional polyolefins, polyesters, acrylics, halogenated hydrocarbons and the like, combinations thereof and laminates. These polymeric films substantially inhibit moisture and oxygen permeation and may be coated with conventional coatings, such as, for example, mineral and mineral oxide coatings that decrease or reduce gas intrusion. The package may comprise a combination of polymer and metal foils, particularly a multi-layer polymer/metal-foil composite, such as a polyester/aluminum foil/ethylacrylic acid laminate.

Nonabsorbable medical devices may be packaged in any of the materials described above. In addition, it is desirable to package nonabsorbable medical devices in a package made of a material that serves as a sterile barrier, such as a porous material, i.e., medical grade paper, or a polymeric film or fabric that is permeable to moisture and gas, i.e., TYVEK® nonwoven material, manufactured by DuPont and made from high-density polyethylene fibers. Preferably, nonabsorbable medical devices are packaged in the same packaging materials that are used for absorbable medical devices, such as hermetically sealed packages, when it is desirable to have antimicrobial medical devices having a shelf life of at least 6 months, preferably at least 1 year and most preferably at least 2 years.

Microorganisms of the genus *Staphylococcus* are the most prevalent of all of the organisms associated with device-related surgical site infection. *S. aureus* and *S. epidermidis* are commonly present on patients' skin and as such are introduced easily into wounds. An efficacious antimicrobial agent against *Staphylococcus* is 2,4,4'-trichloro-2'-hydroxydiphenyl ether. This compound has a minimum inhibitory concentration (MIC) against *S. aureus* of 0.01 ppm, as measured in a suitable growth medium and as described by Bhargava, H. et al in the American Journal of Infection Control, June 1996, pages 209-218. The MIC for a particular antimicrobial agent and a particular microorganism is defined as the minimum concentration of that antimicrobial agent that must be present in an otherwise suitable growth medium for that microorganism, in order to render the growth medium unsuitable for that microorganism, i.e., the minimum concentration to inhibit growth of that microorganism. The phrases "an amount sufficient to substantially inhibit bacterial colonization" and "an effective amount" of the antimicrobial agent, as used herein, are defined as the minimum inhibitory concentration for *S. aureus* or greater.

A demonstration of this MIC is seen in the disk diffusion method of susceptibility. A filter paper disk, or other object, impregnated with a particular antimicrobial agent is applied to an agar medium that is inoculated with the test organism. Where the antimicrobial agent diffuses through the medium, and as long as the concentration of the antimicrobial agent is above the minimum inhibitory concentration (MIC), none of the susceptible organism will grow on or around the disk for some distance. This distance is called a zone of inhibition. Assuming the antimicrobial agent has a diffusion rate in the medium, the presence of a zone of inhibition around a disk impregnated with an antimicrobial agent indicates that the organism is inhibited by the presence of the antimicrobial agent in the otherwise satisfactory growth medium. The diameter of the zone of inhibition is inversely proportional to the MIC.

Method for Making an Antimicrobial Medical Device

In accordance with various methods of the present invention, a medical device is directly exposed to the antimicrobial agent, i.e., the antimicrobial agent source is located in the package having the medical device. For example, the package may contain an antimicrobial agent source, may have an antimicrobial agent source attached to the inner surface of the package, or the antimicrobial agent source may be integral with one or more packaging component in the package or with the package itself. In these embodiments, the medical device is positioned within the package and may initially be free of an antimicrobial agent or may initially comprise one or more surfaces having an antimicrobial agent disposed thereon. The package, the antimicrobial agent source and the medical device are then subjected to time, temperature and pressure conditions sufficient to vapor transfer an effective amount of the antimicrobial agent from the antimicrobial agent source to the medical device, thereby substantially inhibiting bacterial colonization on the medical device.

In the case where the medical device is initially free of an antimicrobial agent, the antimicrobial agent is delivered to the medical device from an antimicrobial agent source when the package, the antimicrobial agent source and the medical device are subjected to time, temperature and pressure conditions sufficient to vapor transfer a portion of the antimicrobial agent from the antimicrobial agent source to the medical device.

In the case where the medical device initially comprises one or more surfaces having an antimicrobial agent disposed thereon, the time, temperature and pressure conditions are sufficient to vapor transfer a portion of each of the antimicrobial agent disposed on the medical device and the antimicrobial agent in the antimicrobial agent source to the inner surface of the package, such that an effective amount of the antimicrobial agent is retained on the medical device, thereby substantially inhibiting bacterial colonization on the medical device and the inner surface of the package. In this embodiment, the amount or concentration of antimicrobial agent on the medical device is stabilized by providing additional antimicrobial agent in the packaging environment.

Alternatively, the medical device may be positioned within a package, and the package having the medical device is exposed indirectly to an external antimicrobial agent source, i.e., the antimicrobial agent source is external to the package having the medical device. Specifically, the antimicrobial agent source and the package having the medical device are subjected to time, temperature and pressure conditions sufficient to vapor transfer an effective amount of the antimicrobial agent from the antimicrobial agent source to the medical device within the package, thereby substantially inhibiting bacterial colonization on the medical device. In this embodiment, the package may be made from a material that serves as a sterile barrier, such as a porous material or polymeric film that is permeable to moisture and gas, such that a gaseous antimicrobial agent source is capable of permeating or transmitting as a vapor through the package. For example, the package having the medical device may be placed in a sealed environment, and the antimicrobial agent source may be contained within the sealed environment or may be subsequently introduced to the sealed environment. The antimicrobial agent source may be any vapor form of the antimicrobial agent.

The rate of vapor transfer of an antimicrobial agent such as triclosan from the antimicrobial agent source to the medical device is substantially dependent upon the time, temperature and pressure conditions under which the package and the medical device are processed, stored and handled. For example, FIG. 1 illustrates that triclosan is capable of transferring from a suture to a packaging component (in a closed vial at atmospheric pressure) when the temperature is maintained at 55° C. over a period of time. The conditions to effectively vapor transfer an antimicrobial agent such as triclosan include a closed environment, atmospheric pressure, a temperature of greater than 40° C., for a period of time ranging from 4 to 8 hours. Also included are any combinations of pressure and temperature to render a partial pressure for the antimicrobial agent that is the same as or greater than the partial pressure rendered under the conditions described above, in combination with a period of time sufficient to render an effective amount or concentration of the antimicrobial agent on the medical device, i.e., the minimum inhibitory concentration (MIC) for S. aureus or greater. Specifically, it is known to one of ordinary skill that if the pressure is reduced, the temperature may be reduced to effect the same partial pressure. Alternatively, if the pressure is reduced, and the temperature is held constant, the time required to render an effective amount or concentration of the antimicrobial agent on the medical device may be shortened. Generally, the amount of antimicrobial agent in the antimicrobial agent source is at least that amount which is necessary to deliver the effective amount of the antimicrobial agent on the medical device, when exposed to the conditions described below.

Medical devices typically are sterilized to render microorganisms located thereon substantially non-viable. In particular, sterile is understood in the field of art to mean a minimum sterility assurance level of $10^{-6}$. Examples of sterilization processes are described in U.S. Pat. Nos. 3,815,315, 3,068,864, 3,767,362, 5,464,580, 5,128,101 and 5,868,244, each of which is incorporated herein in its entirety. Specifically, absorbable medical devices may be sensitive to radiation and heat. Accordingly, it may be desirable to sterilize such devices using conventional sterilant gases or agents, such as, for example, ethylene oxide gas.

An ethylene oxide sterilization process is described below, since the time, temperature and pressure conditions sufficient to vapor transfer the antimicrobial agent from the antimicrobial agent source to the medical device, are present in an ethylene oxide sterilization process. However the time, temperature and pressure conditions sufficient to vapor transfer the antimicrobial agent from the antimicrobial agent source to the medical device, may be effected alone or in other types of sterilization processes, and are not limited to an ethylene oxide sterilization process or to sterilization processes in general.

As discussed above, absorbable medical devices are sensitive to moisture and are therefore often packaged in hermetically sealed packages, such as sealed foil packages. However, sealed foil packages are also impervious to sterilant gas. In order to compensate for this and utilize foil packages in ethylene oxide gas sterilization processes, processes have been developed using foil packages having gas permeable or pervious vents (e.g., TYVEK polymer). The gas permeable vents are mounted to an open end of the package and allow the passage of air, water vapor and ethylene oxide into the interior of the package. After the sterilization process is complete, the package is sealed adjacent to the vent so the vent is effectively excluded from the sealed package, and the vent is cut away or otherwise removed, thereby producing a gas impervious hermetically sealed package. Another type of foil package having a vent is a pouch-type package having a vent mounted adjacent to an end of the package, wherein the vent is sealed to one side of the package creating a vented section. After the sterilization process is complete the package is sealed adjacent to the vented section, and the sealed package is cut away for the vented section.

In one embodiment, the antimicrobial agent source is placed within the package, attached to the inner surface of the package, or is integral with one or more packaging component in the package or with the package itself. After the peripheral seal and side seals have been formed in the package, the packaged medical device may be placed into a conventional ethylene oxide sterilization unit. If the package is a foil package, the antimicrobial agent source may be any of the antimicrobial agent sources described above or the antimicrobial agent source may be an antimicrobial agent loaded-gas permeable vent. For example, an antimicrobial agent such as triclosan may be loaded onto a Tyvek gas permeable vent by coating the Tyvek strip with a solution of ethyl acetate and triclosan; the antimicrobial agent loaded gas permeable vent is positioned within a package by mounting it to a hermetic packaging material; the medical device is positioned within the hermetic packaging material; the periphery of the hermetic packaging material is sealed in a manner to enclose the medical device and to allow the passage of gas into the interior of the hermetic packaging material through the vent; the packaging material having the antimicrobial agent loaded gas permeable vent and the medical device is subjected to time, temperature and pressure conditions sufficient to vapor transfer an effective amount of the antimicrobial agent from the antimicrobial agent loaded gas permeable vent to the medical device; the packaging material is sealed to enclose the medical device and exclude the vent; and the vent is cut away to thereby produce an antimicrobial medical device.

In another embodiment, the antimicrobial agent source may be introduced into the sterilization or other unit external to the package having the medical device. For example, the medical device is positioned within the package; the package having the medical device is exposed to an antimicrobial agent source; and the package having the medical device and the antimicrobial agent source is subjected to time, temperature and pressure conditions sufficient to vapor transfer an effective amount of the antimicrobial agent from the antimicrobial agent source to the medical device within the package, thereby substantially inhibiting bacterial colonization on the medical device. The package may be made from a material that serves as a sterile barrier, such as a porous material or a polymeric film that is permeable to moisture and gas, or from a material that results in a hermetically sealed package.

Prior to the start of the cycle, the sterilization unit may be heated to an internal temperature of about 25° C. The sterilization unit is maintained about 22 to 37° C. throughout the humidification and sterilization cycles. Next, a vacuum may be drawn on the sterilization unit to achieve a vacuum of approximately 1.8 to 6.0 kPa.

In a humidification cycle, steam then may be injected to provide a source of water vapor for the product to be sterilized. The packaged medical devices may be exposed to water vapor in the sterilization unit for a period of time of about 60 to 90 minutes. Times may vary, however, depending upon the medical device being sterilized.

Following this humidification portion of the cycle, the sterilization unit may be pressurized by the introduction of dry inert gas, such as nitrogen gas, to a pressure of between about 42 and 48 kPa. Once the desired pressure is reached, pure ethylene oxide may be introduced into the sterilization unit until the pressure reaches about 95 kPa. The ethylene oxide may be maintained for a period of time effective to sterilize the packaged medical device. For example, the ethylene oxide may be maintained in the sterilization unit for about 360 to about 600 minutes for surgical sutures. The time required to sterilize other medical devices may vary depending upon the type of product and the packaging. The ethylene oxide then may be evacuated from the sterilization unit and the unit may be maintained under vacuum at a pressure of approximately 0.07 kPa for approximately 150 to 300 minutes in order to remove residual moisture and ethylene oxide from the sterilized packaged medical devices. The pressure in the sterilization unit may be returned to atmospheric pressure.

The following stage of the process is a drying cycle. The packaged medical device may be dried by exposure to dry nitrogen and vacuum over a number of cycles sufficient to effectively remove residual moisture and water vapor from the packaged medical device to a preselected level. During these cycles, the packaged medical device may be subjected to a number of pressure increases and decreases, at temperatures greater than room temperature. Specifically, the jacket temperature of the drying chamber may be maintained at a temperature of between approximately 53° C. to 57° C. throughout the drying cycle. Higher temperatures, however, may be employed, such as about 65° C. to 70° C. for sutures, and higher depending upon the medical device being sterilized. A typical drying cycle includes the steps of increasing the pressure with nitrogen to approximately 100 kPa, evacuating the chamber to a pressure of approximately 0.07 kPa over a period of 180 to 240 minutes, reintroducing nitrogen to a pressure of 100 kPa and circulating the nitrogen for approximately 90 minutes, evacuating the chamber to a pressure of approximately 0.01 kPa over a period of approximately 240 to 360 minutes and maintaining a pressure of not more than 0.005 kPa for an additional 4 to 96 hours. At the end of the humidification, sterilization and drying cycles, which takes typically about 24 hours, the vessel is returned to ambient pressure with dry nitrogen gas. Once drying to the preselected moisture level is complete, the packaged medical device may be removed from the drying chamber and stored in a humidity controlled storage area.

Upon completion of the sterilization process, the antimicrobial medical device, the package and/or the packaging component have thereon an amount of the antimicrobial agent effective to substantially inhibit colonization of bacteria on or adjacent the antimicrobial device, the package and/or the packaging component. The examples below demonstrate that it is possible to produce an antimicrobial medical device having an effective amount of antimicrobial agent for at least 6 months, preferably for at least 1 year and most preferably for at least 2 years, after sterilization and packaging of the medical device and before its use in a surgical procedure, when a hermetically sealed package is used.

Example 1

27" length of VICRYL® sutures, size 5-0 and dyed (a braided multifilament suture composed of a copolymer made from 90% glycolide and 10% L-lactide, that is commercially available from Ethicon, Inc.), initially substantially free of an antimicrobial agent and positioned in a polypropylene suture tray, were placed in packages having an antimicrobial agent source located therein. In these examples, packaging components, i.e., paper lids made from medical grade, kraft paper, weighing about 0.45 g each and used to cover the suture tray, were coated by dipping the individual lids in a solution containing 5% by weight triclosan in ethyl acetate. Each lid was held in the solution for approximately five seconds, allowed to air dry at room temperature overnight, and then positioned over the suture tray. The triclosan present on each lid ranged from 2-3% by weight of the total weight of the dried lid. The suture assemblies, each having the suture, the suture tray and the triclosan-loaded paper lid, were arranged in separate cavities created in a peelable foil packaging material, i.e., an ethylacrylic acid-coated aluminum foil composite, having a TYVEK® gas permeable vent mounted to an open end of the packaging material to allow the passage of air, water vapor and ethylene oxide into the interior of the cavities within the packaging material. The suture assemblies were then sterilized, which conveniently subjected the suture assemblies to time, temperature and pressure conditions sufficient to vapor transfer an effective amount of the antimicrobial agent from the antimicrobial agent source, i.e., the triclosan-loaded paper lid, to the suture. After the sterilization process was complete, the individual cavities were sealed and the gas permeable vent was effectively excluded to form sealed packages each having a suture assembly contained therein. The sutures were then removed from packages and subjected to zone of inhibition testing.

The data included in the tables below was from zone of inhibition testing performed on the sutures, when challenged with *Staphylococcus. aureus* ATCC 6538; methicillin-resistant *Staphylococcus. epidermidis* ATCC 51625, *Escherichia coli* ATCC 8739, vancomycin resistant *Enterococcus faecium* ATCC 700221, or *Streptococcus agalacticae* ATCC 624, grown in Tryptic Soy broth at 37° C. for 24 h. The culture was diluted in sterile 0.85% saline to create inocula with concentrations of approximately 1,000,000 cfu (colony forming units) per milliliter. For each challenge organism, the suture was aseptically cut into 5-cm pieces. The pieces were placed in separate sterile Petri dishes with 0.1 mL of inoculum. Tryptic Soy agar was poured into the plates, and the plates were incubated at 37° C. for 48 h. Zones of inhibition were read as the distance in millimeters from the suture to the edge of visible growth.

|  | Microbe | n | Min. | Max. | Ave. |
|---|---|---|---|---|---|
| Example 1 | S. aureus | 8 | 15 | 19 | 16 |
|  | E. coli | 8 | 6 | 9 | 7 | n = number of samples tested

Example 2

This example is identical to EXAMPLE 1, except the suture was a PDS® II suture (a monofilament polydioxanone suture that is commercially available from Ethicon, Inc.) and the paper lid was coated by dipping the individual lids in a solution containing 10% by weight triclosan in ethyl acetate.

|  | Microbe | n | Min. | Max. | Ave. |
|---|---|---|---|---|---|
| Example 2 | S. agalachiae | 3 | 0 | 4 | 2 |
|  | S. aureus | 3 | NCP | NCP | NCP |
|  | E. coli | 3 | 11 | 20 | 15 |

NCP = No colonies were remaining on plate

Example 3

This example is identical to EXAMPLE 1, except the suture was a PROLENE® suture (a monofilament polypropylene suture that is commercially available from Ethicon, Inc.) and the paper lid was coated by dipping the individual lids in a solution containing 10% by weight triclosan in ethyl acetate.

|  | Microbe | N | Min. | Max. | Ave. |
|---|---|---|---|---|---|
| Example 3 | S. agalachiae | 3 | 0 | 0 | 0 |
|  | S. aureus | 3 | 17 | 20 | 18 |
|  | E. coli | 3 | 0 | 6 | 2 |

Examples 4-5

The preparation of these samples was identical to the preparation of EXAMPLE 1, except a solution containing 1.1% (Example 4) or 5.6% (Example 5) by weight triclosan, 15% by weight copolymer of glycolide and lactide, and the remainder ethyl acetate, was used as the antimicrobial agent source, instead of the triclosan-loaded paper lid. 0.5 ml of these solutions were placed in separate cavities created in the peelable foil packaging material, i.e., under each suture assembly, and allowed to dry at room temperature overnight, such that Example 4 had 5 mg triclosan in each cavity, while Example 5 had 25 mg of triclosan in each cavity. Then sutures assemblies, each having a 27" suture wound in a polypropylene tray and covered with a paper lid, were placed into the cavities followed by sterilization.

|  | Microbe | Test No. 1 | Test No. 2 | Test No. 3 |
|---|---|---|---|---|
| Example 4 | S. aureus | 5 | 9 | 8 |
|  | S. epidermidis | 6 | 6 | 5 |
|  | E. coli | 0 | 0 | 0 |
|  | Enterococcus Faecium | 0 | 0 | 0 |
|  | S. agalachiae | 0 | 0 | 0 |
| Example 5 | S. aureus | 16 | 13 | 15 |
|  | S. epidermidis | 15 | 20 | 16 |
|  | E. coli | 1 | 6 | 5 |
|  | Enterococcus Faecium | 0 | 0 | 0 |
|  | S. agalachiae | 0 | 0 | 0 |

Examples 4 and 5 show that the use of an antimicrobial agent reservoir in the foil cavity is an effective means of generating a product that exhibits a zone of inhibition when challenged with *S. aureus* and *S. epidermidis*. The table below shows data from a tissue passage study using sutures prepared by the procedure described for Example 5. Specifically, a needle was manually attached to a sterile suture and then passed ten times through a raw chicken breast to determine if the triclosan would be removed. The data shows that significant zones of inhibition still remain after passing the suture through the tissue, when challenged with *S. aureus* and *S. epidermidis*.

|  | Microbe | Test No. 1 |
|---|---|---|
| Example 5a | S. aureus | 15 |
|  | S. epidermidis | 15 |
|  | E. coli | 0 |

Examples 6-7

The preparation of EXAMPLE 6 was identical to the preparation of EXAMPLE 4, while the preparation of EXAMPLE 7 was identical to the preparation of EXAMPLE 5, except the suture was a PDS® II suture.

|  | Microbe | Test No. 1 | Test No. 2 | Test No. 3 |
|---|---|---|---|---|
| Example 6 | S. aureus | 7 | 7 | 6 |
|  | S. epidermidis | 7 | 6 | 6 |
|  | E. coli | 0 | 0 | 0 |
|  | Enterococcus Faecium | 0 | 0 | 0 |
|  | S. agalachiae | 0 | 0 | 0 |
| Example 7 | S. aureus | 12 | 14 | 22 |
|  | S. epidermidis | 14 | 18 | 18 |
|  | E. coli | 3 | 1 | 1 |
|  | Enterococcus Faecium | 0 | 0 | 0 |
|  | S. agalachiae | 0 | 0 | 0 |

Examples 6 and 7 show that the use of an antimicrobial agent reservoir in the foil cavity is an effective means of generating a product that exhibits a zone of inhibition when challenged with S. aureus and S. epidermidis. The table below shows data from a tissue passage study using sutures prepared by the procedure described for Example 7. Specifically, a needle was manually attached to a sterile suture and then passed ten times through a raw chicken breast to determine if the triclosan would be removed. The data shows that significant zones of inhibition still remain after passing the suture through the tissue, when challenged with S. aureus and S. epidermidis.

|  | Microbe | Test No. 1 |
|---|---|---|
| Example 7a | S. aureus | 13 |
|  | S. epidermidis | 15 |
|  | E. coli | 5 |

Examples 8-10

These examples are identical to EXAMPLE 1, except the suture was a dyed VICRYL® Plus suture, size 5-0 (a braided multifilament antimicrobial suture composed of a copolymer made from 90% glycolide and 10% L-lactide, having triclosan contained in a coating mixture composed of a copolymer of glycolide and lactide and calcium stearate and ethyl acetate, that is commercially available from Ethicon, Inc.). Example 8 had 1.0% by weight triclosan in the coating mixture; Example 9 had 2.0%; and Example 10 had 3.0%, based on the total weight of the coating mixture.

|  | Microbe | N | Min. | Max. | Ave. |
|---|---|---|---|---|---|
| Example 8 | S. aureus | 8 | 16 | 19 | 18 |
|  | E. coli | 8 | 7 | 9 | 8 |
| Example 9 | S. aureus | 8 | 15 | 21 | 18 |
|  | E. coli | 8 | 7 | 9 | 8 |
| Example 10 | S. aureus | 8 | 15 | 20 | 17 |
|  | E. coli | 8 | 7 | 10 | 8 |

Examples 11-12

These examples are identical to EXAMPLES 4-5, except the suture was a dyed VICRYL® Plus suture, size 2-0, with 2% by weight triclosan in the coating mixture.

|  | Microbe |  |  |  |
|---|---|---|---|---|
| Example 11 | S. aureus | 17 | 14 | 14 |
|  | S. epidermidis | 15 | 15 | 15 |
|  | E. coli | 1 | 1 | 0 |
|  | Enterococcus Faecium | 0 | 0 | 0 |
|  | S. agalachiae | 0 | 0 | 0 |
| Example 12 | S. aureus | >25 | 25 | 20 |
|  | S. epidermidis | >25 | >25 | 20 |
|  | E. coli | 4 | 4 | 6 |
|  | Enterococcus Faecium | 0 | 0 | 0 |
|  | S. agalachiae | 0 | 0 | 0 |

Example 13

This example is identical to EXAMPLE 1, except that VICRYL® sutures, size 2-0 and dyed, were used and the antimicrobial agent source was a Tyvek® gas permeable strip. One side of a Tyvek strip was manually coated with ethyl acetate containing 20% by weight triclosan. Suture assemblies, each having the suture, a polypropylene suture tray and a paper lid, were arranged in separate cavities created in a peelable foil packaging material having the triclosan-loaded TYVEK® gas permeable strip mounted to an open end of the packaging material to allow the passage of air, water vapor and ethylene oxide into the interior of the cavities within the packaging material. The suture assemblies were sterilized. After the sterilization process was complete, the individual cavities were sealed and the gas permeable vent was effectively excluded to form sealed packages each having a suture assembly contained therein. Thereafter, the sutures were removed from packages and subjected to zone of inhibition testing. Three samples were taken from each suture; all samples showed zones of inhibitions when challenged with S. aureus and S. epidermis.

What is claimed is:

1. A method of making an antimicrobial medical device comprising the steps of:
    positioning a medical device and an antimicrobial agent agent-loaded reservoir within a package comprising an inner surface, said antimicrobial agent being in a dry state and selected from the group consisting of halogenated hydroxyl ethers, acyloxydiphenyl ethers, and combinations thereof;
    subjecting the package, the antimicrobial agent-loaded reservoir and the medical device to time, temperature and pressure conditions sufficient to vapor transfer an effective amount of the antimicrobial agent from the antimicrobial agent-loaded reservoir to the medical device, thereby substantially inhibiting bacterial colonization on the medical device.

2. The method of claim 1, where an effective amount of the antimicrobial agent is vapor transferred from the antimicrobial agent-loaded reservoir to the inner surface of the package, thereby substantially inhibiting bacterial colonization on the package.

3. The method of claim 2, wherein the antimicrobial agent-loaded reservoir is positioned within the package.

4. The method of claim 2, where the antimicrobial agent-loaded reservoir is on the inner surface of the package.

5. The method of claim 2, wherein the antimicrobial agent-loaded reservoir is integral with one or more packaging components in the package or the package.

6. The method according to claim 1, wherein the medical device further comprises at least one active agent selected from the group consisting of a biocide, a disinfectant, an antiseptic, an antibiotic, an antimicrobial peptide, a lytic bacteriophage, a surfactant; an adhesion blocker; an oligonucleotide, an efflux pump inhibitors; a photosensitive dye, an immune modulator and a chelator.

7. The method according to claim 1, wherein the antimicrobial agent-loaded reservoir is a porous material coated or impregnated with said dry antimicrobial agent.

8. The method according to claim 7, wherein the porous material is selected from the group consisting of paper, sponge or foam.

9. A method for making an antimicrobial suture comprising the steps of:
- positioning a suture and an antimicrobial agent-loaded reservoir within a package, said antimicrobial agent being in a dry state and selected from the group consisting of halogenated hydroxyl ethers, acyloxydiphenyl ethers, and combinations thereof; and
- subjecting the package, the suture and the antimicrobial agent-loaded reservoir to time, temperature and pressure conditions sufficient to vapor transfer an effective amount of the antimicrobial agent from the antimicrobial agent-loaded reservoir to the suture, thereby substantially inhibiting bacterial colonization on the suture.

10. The method of claim 9, where an effective amount of the antimicrobial agent is vapor transferred from the antimicrobial agent-loaded reservoir to the inner surface of the package, thereby substantially inhibiting bacterial colonization on the package.

11. The method according to claim 1, wherein the suture further comprises at least one active agent selected from the group consisting of a biocide, a disinfectant, an antiseptic, an antibiotic, an antimicrobial peptide, a lytic bacteriophage, a surfactant; an adhesion blocker; an oligonucleotide, an efflux pump inhibitors; a photosensitive dye, an immune modulator and a chelator.

12. The method according to claim 9, wherein the antimicrobial agent-loaded reservoir is a porous material coated or impregnated with said dry antimicrobial agent.

13. The method according to claim 12, wherein the porous material is selected from the group consisting of paper, sponge or foam.

* * * * *